United States Patent [19]

Gordon

[11] 4,039,661

[45] Aug. 2, 1977

[54] ANTIBIOTIC METHOD OF TREATING BENIGN PROSTATIC HYPERTROPHY WITH SCH-16656

[75] Inventor: Harry W. Gordon, Bronx County, N.Y.

[73] Assignee: Schmid Laboratories, Inc., Little Falls, N.J.

[21] Appl. No.: 628,790

[22] Filed: Nov. 4, 1975

Related U.S. Application Data

[60] Continuation-in-part of Ser. No. 584,607, June 6, 1975, abandoned, which is a continuation of Ser. No. 414,968, Nov. 23, 1973, Pat. No. 3,920,813, which is a continuation of Ser. No. 313,568, Dec. 8, 1972, Pat. No. 3,843,785, which is a continuation of Ser. No. 194,052, Oct. 29, 1971, Pat. No. 3,721,734, which is a division of Ser. No. 70,509, Sept. 8, 1970, Pat. No. 3,714,347, which is a continuation-in-part of Ser. No. 544,712, April 25, 1966, abandoned, which is a continuation of Ser. No. 623,847, March 17, 1967, Pat. No. 3,584,118.

[51] Int. Cl.² ............................................. A61K 35/00
[52] U.S. Cl. .................................... 424/119; 424/115
[58] Field of Search ................................ 424/115, 119

[56] References Cited

PUBLICATIONS

Wagman et al., Antimicrobial Agents and Chemotherapy Apr. 1975, pp. 457–461.

Primary Examiner—Jerome D. Goldberg
Attorney, Agent, or Firm—Darby & Darby

[57] ABSTRACT

Orally administered compositions for treating prostatic hypertrophy are described herein. These compositions contain an effective dose of a pharmaceutical formulation containing antibiotic SCH-16656. Also, the method of treating prostatic hypertrophy with such compositions is described herein.

3 Claims, No Drawings

ANTIBIOTIC METHOD OF TREATING BENIGN PROSTATIC HYPERTROPHY WITH SCH-16656

This application is a continuation-in-part of application Ser. No. 584,607 filed June 6, 1975 now abandoned, which is a continuation of copending application Ser. No. 414,968, filed Nov. 23, 1973 now U.S. Pat. No. 3,920,813, which is a continuation of copending application Ser. No. 313,568, filed Dec. 8, 1972 now U.S. Pat. No. 3,843,785, which is a continuation of application Ser. No. 194,052, filed Oct 29, 1971 now U.S. Pat. No. 3,721,734, which is a divisional of application Ser. No. 70,509, filed Sept. 8, 1970 now Pat. No. 3,714,347, which is a continuation-in-part of copending application Ser. No. 544,712, filed Apr. 25, 1966, now abandoned, and a continuation of application Ser. No. 623,847, filed March 17, 1967, now U.S. Pat. No. 3,584,118.

This invention relates to a composition containing a polyenic macrolide compound and the method of treating prostatic hypertrophy by orally administering the same.

It is known that prostatic hypertrophy may in limited cases be treated by the administration of hormones such as steroids. However, the treatment with steroids or other hormones is severely restricted since its effect is related to the suppression of the secretion of a gonadotrophic substance by the adrenal cortex. Further, the administration of a hormone carries with it extensive physiological effects on the organ and organ systems in addition to the prostate. Therefore, there has not been available a composition for the treatment of prostatic hypertrophy which has a broad spectrum of effectiveness independent of the cause of the prostatic hypertrophy.

A great number of polyenic macrolide antibiotic compounds are known today which are used or proposed for use as antifungal chemotherapeutic agents and which have been the subject of extensive scientific investigation in past years. Biologically, the polyene macrolide antibiotics have been recognized to be potent chemotherapeutic agents against a wide variety of yeasts and fungi. However, the use of these polyenic macrolide compounds for the treatment of certain fungal infections has been limited by their poor oral absorption from the gastrointestinal tract. The application of these polyenic macrolide antibiotic compounds has been restricted primarily to topical use.

It has now been unexpectedly discovered that the oral administration of a polyenic macrolide composition, has a selective effect on the prostate gland in mammals which does not appear to express its effect by stimulating or suppressing hormonal producing endocrine glands. Its effect on the prostate is carried out by reducing its size and altering its hypertrophic histological picture and texture to that of a normal appearing gland. This effect is believed not due to the antibiotic function of these polyenic macrolide compounds but apparently to their chemical structure.

Accordingly, one aspect of the present invention is to provide a method for the treatment of prostatic hypertrophy which comprises orally administering an effective dose of antibiotic SCH-16656 a specific known polyenic macrolide compound.

Another aspect of the present invention is to provide an orally administered composition for the treatment of prostatic hypertrophy which composition comprises a pharmaceutical formulation comprising an effective dose of antibiotic SCH-16656 a specific known polyenic macrolide compound.

An additional aspect of the present invention is to provide an enteric tablet or capsule containing an effective dose of a composition of the present invention for the treatment of prostatic hypertrophy.

Other aspects of the invention will be apparent from the following detailed description.

According to the present invention, the compositions found effective for the treatment of prostate hypertrophy in mammals comprise antibiotic SCH-16656, a polyenic macrolidic composition. Since the polyenic compounds were first discovered in 1950, a large body of literature has become available describing the extensive chemical investigation of these compounds and demonstrating that they possess generally similar chemical properties. The present broad classification of the polyenic macrolide compounds is due to the work of Oroshnik et al, in 1955 (see Polyene Antibiotics, Science, Vol. 121, pp. 147-149). In 1955 only 9 polyenic macrolide compounds had been isolated in reasonably pure form but since then well over 50 polyenic macrolide compounds have been reported. Undoubtedly some of these polyenes have been reported more than once under different names.

The known polyenic macrolide compounds with one or two exceptions have been produced as antibiotics by cultivation of Streptomyces in different media and by extraction of the substances from these cultures. It has been demonstrated in the literature that the known polyenic compounds are (1) of fairly high molecular weight (ca. 700-1500), (2) contain macrocyclic lactones, better known as macrolides (hereinafter referred to as "polyenic macrolide compounds"), and (3) each possess a chromophore in the nucleus of from four to seven conjugated double bonds (tetraenes, pentaenes, hexaenes, and heptaenes) identified by examination of their ultraviolet absorption spectra. These conjugated systems are generally unsubstituted (except the methyl pentaenes) and either of the "all-trans" or "cis-trans" configuration. Based on the evidence available to date, it is indicated that the known polyenic macrolide compounds contain a twenty-six to a thirty-seven membered lactone ring wherein all of the ring atoms except the single oxygen atom are carbons. The evidence to date also indicates that only C, H, O, and N are present in the known polyenic macrolide compounds.

Any single known polyenic macrolide compound may have substituents linked to the ring such as amino sugars and N-acyl derivatives thereof, aromatic amines and N-acyl derivatives thereof, carboxyls, methyls, carbonyls, aliphatics, hydroxy aliphatics and epoxies. The majority of the polyenic macrolides are amphoteric substances. The acidity of these polyenes is due to a carboxyl group and the basicity of the amphoteric polyenes is due to the presence of an amino sugar known as mycosamine (3-amino 3,6 dideoxy-D-mannose), or perosamine (4-amino 4,6 dideoxy-D-mannose). The basicity may also be due to the additional presence of aromatic amino moieties. Some polyene macrolides such as filipin, lagosin and fungichromin are neutral. The substitution of the amine function with such organic radicals as acyl groups reduces the effectiveness of the macrolide nucleus in the treatment of prostate hypertrophy but does not destroy this activity. The acylation results in neutralization of the basic properties and improved solubilities of the N-acylated derivative in various media, such as organic solvents, and readily permits the formation of water soluble salts, as fully described in U.S. Pat. No. 3,244,590.

The following articles should be consulted for references to the discovery, isolation and chemical properties of the polyenic macrolide compounds:

1. Vining, "The Polyene Antifungal Antibiotics" Hindustan Antibiotics Bull., Vol. 3, pp 32–54 (1960).
2. Waksman et al, "The Actinomycetes, Vol. III, Antibiotics of Actinomycetes" (Williams and Wilkins, Baltimore, 1962).
3. Droughet, "Noveaux Antibiotiques Antifongiques"Symp. Int. Chimiotherapie, Naples, 1961, pp 21–50 (1963).
4. W. Oroshnik et al, "Fortschritte der Chemie Organischer Naturstoffe" Vol. XXI, pp 18–79 (1963).

The general class of polyenic macrolide compounds which have been described above and to which the present invention is applicable will now be discussed in greater detail by reference to the four distinct classes of polyenic macrolide compounds, that is, tetraenes, pentaenes, hexaenes and heptaenes, and to the substances that fall within each of these separate classifications.

The heptaene group of polyene macrolides are classifiable into at least five groups which may be correspondingly identified as follows:

A. Aromatic I - Identified as those compounds containing the heptaene macrolide nucleus, one carboxyl group, a single amino sugar moiety (mycosamine) glycosidically linked to the macrolide nucleus and an aromatic amino moiety (p-aminophenyl) aldolically linked to the macrolide nucleus. Representatives of this group are (a) candicidin which may possibly be identical to trichamycin A, hamycin (minor component), heptamycin, ascosin and levorin $A_2$; (b) trichomycin B which may possibly be identical to levorin $A_3$, hamycin (major component) and PA-150; and (c) levorin A. Antibiotic SCH 16656 produced by Actinoplanes sp. NRRL-5325 (deposited in the culture collection of the Northern Utilization Research and Development Division of the U.S. Department of Agriculture) is also representative of this group.

B. Aromatic II - Identified as those compounds contaning the heptaene macrolide nucleus, one carboxyl group, an amino sugar (mycosamine) glycosidically linked to the macrolide nucleus, and an aromatic amino moiety (N-methyl-p-aminophenyl) aldolically linked to the macrolide nucleus. Representative polyenic macrolides of this group are: (a) candimycin, and (b) hamycin (minor component of hamycin complex).

C. Aromatic III - Identified as those compounds containing the heptaene macrolide nucleus, an aromatic amino moiety (N-methyl-p-aminophenyl), aldolically linked to the macrolide nucleus, and an amino sugar (perosamine), glycosidically linked to the macrolide nucleus. It is noted that the aromatic amino moiety just identified has previously been incorrectly reported in the literature as a p-aminobenzyl moiety. Representative of this group is fungimycin. This substance was originally styled by antibiotic number NC 1968 and for a brief interval identified as perimycin and aminomycin.

D. Non-Aromatic - Identified as those compounds containing the heptaene macrolide nucleus, one carboxyl moiety and a single amino sugar (mycosamine), glycosidically linked to the macrolide nucleus. Representative of this group are: (a) candidin; (b) candidinin; (c) candidoin; (d) amphotericin B; (e) mycoheptin; (f) levorin B; and (g) antibiotic F-17-C.

E. Poorly Defined Heptaenes: A number of heptaene macrolide compounds have been described in the literature but have not as yet been sufficiently characterized as to all the substituents linked to the polyenic macrolide nucleus. These heptaene macrolides are Streptomyces abikoensis heptaene, aureofacin, antibiotic 757, ayfactin A, ayfactin B, antifungin 4915, eurotin A, antibiotic AE-56, antibiotic 2814-H, grubilin, monicamycin, antibiotics A, B, and C from streptomyces species related to S. viridans.

It will be understood that where a polyenic macrolide compound of the class herein described is identical with one of the above named compounds, but has been known by another name by reason of independent production or production in accompaniment to other antibiotics, the identification of such substances by the name set forth above is intended to mean the same compound under all other designations.

In the preparation and administration of dosages, a variety of pharmaceutical formulations may be employed, such as capsules, or tablets, preferably in enteric form. The quantity of effective dose supplied by each capsule or tablet is relatively unimportant since the total dosage can be reached by administration of either one or a plurality of capsules or tablets or both. The capsules employed may compose any well known pharmaceutically acceptable material, such as gelatin, cellulose derivatives, etc. The tablets may be formulated in accordance with conventional procedure employing solid carriers, lubricants, etc., well known in the art. Examples of solid carriers are: starch, sugar, bentonite and other commonly used carriers.

The following examples illustrate suitable pharmaceutical formulations containing the compounds of this invention.

EXAMPLE 1

Hard gelatin capsule available from the Robin Pharmacal Corporation(size 00) is filled with about 0.83 grams of lactose (Fast Flow available from Foremost Dairies, Inc.) and about 100 mg. of active material, the lactose and active ingredient being triturated together in a pestle and mortar until a very fine yellow amorphous powder resulted, prior to filling of the capsule. Obviously, any desired number of capsules may be filled by mixing together any amount of lactose and active ingredient in the same weight ratio indicated above so that each capsule will contain 100 mg. active ingredient; and the quantity of active ingredient may be altered, as desired, by varying the weight ratio of the indicated materials.

EXAMPLE 2

125 g. of corn starch and 2112.5 g. lactose are dried at 140° F for 12 hours before compounding. After drying, each of these materials is sifted through a No. 14 mesh stainless steel screen. The sifted corn starch and lactose are thoroughly mixed for 30 minutes and to this mixture there is added a blended mixture of 250 g. active ingredient and 12.5 g. magnesium stearate. This admixture is blended and then compressed on a tableting machine into 5000 substantially round tablets each containing 50 mg. active ingredient and weighing about 500 mg.

EXAMPLE 3

Enteric tablets for use in this invention may be formulated as follows:

16 g. of powdered corn starch (U.S.P. quality) is dried at 120° F for 12 hours and passed through a No. 25 mesh stainless steel screen. The sifted corn starch is then mixed with 255 g. of anhydrous lactose (direct tablet grade). To this mixture, 4 g. of magnesium stearate is added followed by 50 g. of the active ingredient. These materials are then mixed in a small pebble mill for 30 minutes and compressed on a single punch machine producing 1,000 tablets, each containing 50 mg. active ingredient. Each tablet weighs approximately 325 mg. The average hardness is 6, as measured on a Monsanto Hardness Tester.

The tablets are then placed in a coating pan rotating at 29 r.p.m. and subjected to warm air of approximately 80° F for about 10 minutes. Then 30 cc's of a pharmaceutical glazed composition is applied, this composition being refined wax and rosin free orange flake shellac with anhydrous alcohol as the medium therefor. Talcum (U.S.P.) or similar dusting powder is applied to the tablets to prevent the tablets from sticking to each other or to the pan and this procedure is followed after the application of each coat to the tablets. The coat is allowed to dry for approximately one hour. Thereafter three additional coats are applied in a similar manner, each coat comprising 30 cc's of the pharmaceutical glaze, with approximately one hour of drying time between the application of successive coats. After four coats are applied the tablets are dried overnight at room temperature and then four more coats are applied in the same manner using the same composition. Each coat is allowed to air dry for 3 hours before applying the next coat. Each of the 8 coats of the enteric tablets is approximately 0.001 inch in thickness. Obviously, the thickness of the coating can be controlled by varying the concentration of the pharmaceutical glaze in the alcohol medium.

The enteric tablets are tested in accordance with the in vitro disintegration test for enteric-coated tablets described in U.S.P. XVII and were found to pass this test.

While the number of coats used in the example heretofore described is 8, it will be appreciated that there are many factors to be considered which permit variation in the number of coats, including the size and shape of the tablets or capsules, the type of coat or combination of coats, etc.

Other procedures and materials well known in the prior art may be employed to prepare suitable enteric coatings. The selection of the coating substance is governed to a large extent by pH and enzyme considerations and the desire to have the enteric composition disintegrate or dissolve when it reaches the duodenum region of the intestinal tract and not in the stomach. The disintegration or dissolution of an enteric coating in the intestinal tract usually depends on several factors, the most important of which are (1) the presence of acidic groups in the enteric substance which cause it to be insoluble in the low pH environment of the stomach but soluble in the intestinal tract due to the higher (but usually not alkali) pH of the media there, and (2) the resistance of the coating to attack by oral and gastric enzymes.

Illustrative of other well known substances that may be used for the enteric coating are the following: cellulose acetate phthalate with resinous carrier; cellulose acetate phthalate-tolu balsam-shellac; cellulose acetate phthalate with fats and waxes; shellac-castor oil; ammoniated shellac; shellac-stearic acid-tolu balsam; stearic acid-castor oil over shellac-silica gel, cellulose acetate phthalates with or without plasticizer and dusting powder(s); acid phthalates of glucose, fructose, etc; ternary copolymers of styrene, methacrylic acid and butyl half-ester of maleic acid; alkyd resin-unsaturated fatty acids-shellac; polyvinyl acid phthalate, etc.

For a description of the procedure for manufacturing enteric formulations such as those exemplified heretofore, reference should be made to U.S. Pat. Nos. 2,196,768; 2,433,244; 2,455,790; 2,540,979; 2,858,252; 3,080,346 and British Pat. Nos. 760,403 and 820,495.

The effectiveness of the compounds of this invention in treating prostatic hypertrophy has been confirmed by tests in large mammals, i.e., those weighing at least about 1 kilogram. For example, tests were conducted on dogs to demonstrate the effectiveness of the polyenic macrolide compounds in reducing the size of the prostate gland.

In one study, ten dogs were used to determine the action of candicidin, the results of which are reported in Table I below.

Each dog was examined for the gross presence of prostatic hypertrophy by palpation. All of the dogs, with the exception of two, were at least ten years of age. The dogs were housed under kennel conditions for a week prior to the oral administration of candicidin. During the acclimatization period the dogs became adjusted to the feeding and kennel routine. A thorough examination of the dogs, including electrocardiography, was undertaken during the acclimatization period. Four of the dogs exhibited a cardiac condition, not unusual for older dogs, which was confirmed by electrocardiography and subsequently at necropsy. This cardiac condition did not affect the course of the experimental trial and indeed was helpful in establishing that even in the presence of such a condition candicidin may be safely administered.

After the one week acclimatization period, a surgical laparotomy was performed on each of the dogs under general anesthesia. The prostate gland was measured in three dimensions, lateral, cranial-caudal and dorsal-ventral and was palpated to determine its consistency. Visual observation of the bladder, intestines, the caudal pole of the kidney, and spleen were made, and the palpation of the liver and kidney was accomplished. In all but three of the dogs a punch biopsy of the prostate was taken. The biopsy specimen taken from the left hemisphere of the prostate gland was fixed in formalin for histological and microscopic examination. The omission of a biopsy in three dogs was instituted as a control to determine whether the trauma of taking the biopsy of the prostate gland might have some influence on inflammation and size of prostatic tissue. In addition, blood and urine specimens were taken for candicidin assay and routine examination.

The dogs were permitted to recover from the surgical laparotomy following which each of the dogs was placed on a regimen of oral administration of candicidin in accordance with the schedule of dose administration given in Table I below. The drug was administered in a hard gelatin capsule in the animal feed.

TABLE I

| Dog No. | Procedure | Age (years) | Daily Dosage (mg) | Dose Days | Animal Body Weight (lbs) | Prostate Size*** Lateral mm | Prostate Size*** Cranial-Caudal (mm) | Prostate Size*** Dorsal-Ventral | % Decrease In Gland Size From Initial Volume |
|---|---|---|---|---|---|---|---|---|---|
| 1 | 1st Laparotomy | 10–13 | | | 53 | 45 | 35 | 40 | |
| | 2nd Laparotomy | | 100* | 30 | 40 | 40 | 35 | 40 | 11.0 |
| | Autopsy | | 200* | 20 | 41 | 42 | 45 | 31 | 7 |
| 2 | 1st Laparotomy | 4 | | | 25 | 20 | 20 | 15 | |
| | 2nd Laparotomy | | 100* | 30 | 20 | 17 | 17 | 10 | 51.5 |
| | Autopsy | | 0** | 20 | 20 | 17 | 19 | 14 | 24.5 |
| 3 | 1st Laparotomy | 13 | | | 55 | 26 | 30 | 25 | |
| | 2nd Laparotomy | | 100* | 30 | 44 | 26 | 30 | 22 | 12.0 |
| | Autopsy | | 400** | 14 | 36 | 26 | 25 | 25 | 17.0 |
| 4 | 1st Laparotomy | 10 | | | 72 | 50 | 50 | 40 | |
| | 2nd Laparotomy | | 100* | 30 | 61 | 41 | 39 | 32 | 48.8 |
| | Autopsy | | 600** | 14 | 50 | 35 | 35 | 27 | 77 |
| 5 | 1st Laparotomy | 17 | | | 32 | 40 | 40 | 30 | 47.0 |
| | Autopsy | | 200* | 30 | 20 | 34 | 25 | 30 | |
| 6 | 1st Laparotomy | 10 | | | 39 | 37 | 30 | 28 | 8.5 |
| | Autopsy | | 300* | 30 | 25 | 34 | 35 | 25 | |
| 7[a] | 1st Laparotomy | 8 | | | 33 | 37 | 26 | 25 | 21.0 |
| | Autopsy | | 300* | 30 | 28 | 27 | 26 | 27 | |
| 8[a] | 1st Laparotomy | 15+ | | | 30 | 60 | 50–55 | 45 | 26.5 |
| | Autopsy | | 300* | 5 | — | 55 | 45–50 | 40 | |
| 9[a] | 1st Laparotomy | 11–13 | | | 30 | 42 | 42 | 34 | 65.0 |
| | Autopsy | | 300* | 30 | 20 | 30 | 28 | 25 | |
| 10 | 1st Laparotomy | 10–11 | | | 34 | 35 | 28 | 28 | 67.2 |
| | Autopsy | | 300* | 30 | 25 | 22 | 24 | 17 | |

*The daily dosage administered after the first laparotomy.
**The daily dosage administered after the second laparotomy.
***The Prostate volume is approximated by multiplying the three dimensions indicated.
[a]No biopsy taken.

As indicated in Table I a second surgical laparotomy was performed on four of the ten dogs in lieu of autopsy because there four dogs were subsequently continued on an altered dose of candicidin to determine whether increase of the drug dose or discontinuance of dosage would further affect prostate size. The remaining six dogs were sacrificed and autopsied after completion of the administration of candicidin. The four dogs on which a second laparotomy was performed were autopsied after completion of the administration of candicidin for the period specified in the above table.

At the time of the second laparotomy and at necropsy the prostate gland was measured and biopsy specimens of the prostate gland of each dog were taken, with the exception of the three dogs indicated in the table for which no biopsy specimens were taken.

In addition, at necropsy, histologic specimens were taken of the general organs — prostate, bladder, pancreas, kidney, adrenal, liver, spleen, testes, intestines, caecum, lung, thyroid and heart for further microscopic examination in order to determine whether any toxic reactions had occurred. All tissues taken were formalin fixed and prepared for microscopic examination. The histologic study of the organs listed did not reveal any evidence of drug toxicity.

At necropsy, blood and urine samples were obtained for assay. The assay method was essentially the procedure described for the assay of Nystatin-Candicidin in "Assay Methods of Antibiotics" 1955, a laboratory method, Donald C. Grove and William D. Randall, pp. 116–119: Method 2. The samples of dog serum and urine investigated microbiologically showed no antifungal activity. The assay tests establish the absence of candicidin in the blood and urine of the test animals.

As shown in the above table, the trauma induced by taking of a biopsy of the prostate gland was not the cause of the reduction in the size of the prostatic tissue. The gross appearance and measurements of the prostate gland taken prior to the administration of candicidin and at laparotomies performed after the drug had been administered revealed a marked reduction of the size of the prostate gland and normal consistency of the gland which is consistent with a significantly younger age of dog. Microscopic examination of the biopsy specimens of the prostate gland on each dog taken at each of the surgical procedures performed confirmed the gross observation of normal appearance and a substantial reduction of size.

The histologic evaluation of the prostate biopsies of dogs taken prior to candicidin administration and at laparotomies did not reveal any cytotoxicity in the gland. The enlarged prostate gland prior to drug administration is characterized by considerable epithelial tufting or papillation; cells are tall, columnar with granular cytoplasm, and gland acini are compressed. The marked reduction in the size of the prostate gland after candicidin administration is accompanied by a decrease in the size of the columnar epithelial cells which are mostly cuboidal; diminished or absent granularity; and papillations are reduced or absent.

As indicated in the above table, body weight loss does not appear to be related in any quantitive way to the dose of the drug administered since the dogs that received 100 mg/day showed a body weight loss no less than those animals receiving a higher dosage. The data also show that a short time of administration, as noted with dog No. 8 of a relative high dose, 300 mg daily, for five days, effected a significant reduction in size of the prostate gland. In the case of dog No. 2, candicidin administration was discontinued after the second laparotomy as indicated in the table and after an additional 20 days of absence of drug administration, it was found that the prostate gland began to increase in size and had achieved about a fifty percent return towards the volume noted at the start of the experiment. However, in this dog the prostate gland was not initially pathologically enlarged.

In some of the dogs diarrhea and vomiting occurred upon the oral administration of candicidin but these effects appeared to be overcome when the dogs were fed a supplement of vitamin B-complex and lactobacilli.

Similar tests were conducted on dogs using nystatin (a tetraene). The gross appearance and measurements of the prostate gland taken prior to the admininstration of nystatin and at laparotomies performed after the drug had been admininstered also revealed a reduction in size of the prostate gland but to a lesser extent than the candicidin treated dogs.

Other tests conducted with polyenic macrolide compounds in mammals appear to indicate that the larger the chromophore in the macrolide nucleus the more effective is the compound in treating prostatic hypertrophy. Accordingly, the heptaene macrolide compounds are preferably used because they have been found to generally give the best results whereas the tetraene macrolide compounds, generally, are least effective in reducing the size of the prostate gland.

It is also indicated that cleavage or other alteration of the macrolide nucleus which opens the lactone ring will destroy the activity of the compounds as will alteration of the chromophore present in the nucleus by total hydrogenation.

Since no one of the substituents found in the polyenic macrolide compounds such as amino sugars, aromatic amines, carboxyls, carbonyls, methyls, aliphatics, epoxies, etc., occurs in all of the polyenic macrolide compounds described herein, this suggests that these substituents, except for the hydroxyl function, are not essential for achieving a reduction in the size of the prostate gland, but rather that the active structure is the macrolide ring containing a conjugated chromophore portion (lipophilic section) and the flexible hydrophilic portion.

Tests conducted with various polyene macrolide compounds including filipin, amphotericin B and fungimycin, indicate that the side chain groups commonly found in the polyenic macrolide compounds are not essential to activity for treating prostate hypertrophy.

It is preferred, commensurate with the desideratum of obtaining the highest degree of effectiveness of the compositions of this invention per given dose of active ingredient, to use an enteric tablet or capsule. Thus when using a specific known polyene macrolide compound in the form of an enteric solid, the entire compound will remain intact when it reaches the intestinal tract so long as the enteric coating composition retains its integrity in the stomach. On the other hand, admininstration of the same dose in a standard solid pharmaceutical formulation may result in a cleavage of any amino sugar present, or of other groups similarly sensitive to gastric conditions. Such cleavage may further result in alteration of the polyenic macrolide nucleus, thereby diminishing the effectiveness of the active ingredient.

The effective dosage of the compounds of this invention depends upon the severity of condition, the stage and the individual characteristics of each mammal being treated. It is expected that the compositions will generally be administered in a dosage range from about 1 mg to about 100 mg active ingredient per kg of body weight per day and preferably from about 5 mg to about 40 mg per kg of body weight per day.

What is claimed is:

1. A process for treating benign prostatic hypertrophy in a mammal afflicted with benign prostatic hypertrophy which comprises orally administering to said mammal an effective amount for treating benign prostatic hypertrophy of antibiotic SCH-16656.

2. The process as defined in claim 1 wherein said effective amount comprises from about 1 mg. to about 100 mg. of antibiotic SCH-16656 per kg. of body weight per day.

3. The process as defined in claim 2 wherein said effective amount comprises from about 5 mg. to about 40 mg. of antibiotic SCH-16656 per kg. of body weight per day.

* * * * *